United States Patent [19]

Sandel

[11] 4,024,870

[45] May 24, 1977

[54] NO-TEAR TOWEL CLAMP

[76] Inventor: Dan Sandel, 17000 Cotter Place, Encino, Calif. 91436

[22] Filed: Dec. 31, 1975

[21] Appl. No.: 645,621

[52] U.S. Cl. .............................. 128/321; 81/425 R; 128/346
[51] Int. Cl.² ......................................... A61B 17/28
[58] Field of Search ............ 81/425 A, 425 R, 426; 128/321, 346

[56] References Cited

UNITED STATES PATENTS

| | | | |
|---|---|---|---|
| 644,932 | 3/1900 | Miller | 128/321 UX |
| 3,209,753 | 10/1965 | Hawkins et al. | 128/321 |
| 3,646,939 | 3/1972 | Sklar | 128/321 |
| 3,786,815 | 1/1974 | Ericson | 128/321 |

*Primary Examiner*—Channing L. Pace
*Attorney, Agent, or Firm*—Poms, Smith, Lande & Glenny

[57] ABSTRACT

A surgical towel and drape clamp having opposed jaw members connected to and opened and closed by the action of pivotally interconnected shank members having finger loop members and locking ratchet members is provided with tip means on one of said jaw members having a blunt distal end portion, the other of said jaw members being provided with tip means having a concave distal end portion which has a peripheral blunt edge. Upon placing a surgical towel or surgical drape between the tip means of said jaw members and manipulating the finger loops to close the jaw members and bring the locking ratchets into interengagement with each other, the surgical towel or surgical drape is trapped between the blunt distal end portion of one of the tip means and the concave distal end portion of the other tip means. The blunt distal end portion of one of the tip means and the peripheral blunt edge of the concave distal end portion of the other tip means preclude any puncturing, abrading and cutting of the surgical towel or surgical drape by the clamping action of the present invention.

2 Claims, 6 Drawing Figures

NO-TEAR TOWEL CLAMP

BACKGROUND OF THE INVENTION

This invention relates in general to clamping devices for use in holding and fastening surgical towels and surgical drapes for use in hospital operating rooms.

Previous devices for clamping, fastening and holding of surgical towels and surgical drapes have effected this result by having opposing jaws which penetrate the towel and drape material and essentially hook it together. Examples of these prior devices are the conventional Backhaus Towel Clamp and the Lorna Towel Clamp. In using the conventional towel clamps, the surgical towel and surgical drape material is perforated each time the device is used. Additionally, the conventional clamps cause the surgical towel or surgical drape to tear. As it is desirable for the surgical drape in particular to be impervious to moisture, the puncturing and/or tearing of the surgical drape is not desirable as these holes and/or rips then allow fluids to pass through the drape.

It has therefore been recognized that a non-penetrating non-tearing towel clamp which will reliably and securely hold and clamp surgical towels and drapes is needed.

SUMMARY OF THE INVENTION

It is therefore a primary object of the present invention to disclose and provide an improvement in surgical towel and drape clamps which will securely and reliably hold and clamp surgical towels and drapes without perforating and tearing such surgical towel and drape material.

It is a further object of the present invention to disclose and provide an improvement in surgical towel and drape clamp jaw members which will permit mating interengagement between the tips of the jaw members while holding and clamping surgical towels and drapes and which, at the same time, will neither cut nor abrade the surgical towel and drape material.

Generally stated, surgical towel and drape clamps have opposing jaw members connected to and opened and closed by the action of pivotally connected shank members having finger loop members and locking ratchet members and said jaw members further are provided with tip means for holding and clamping surgical drapes, surgical towels and the like. The within invention includes the provision of a blunt distal end portion on one of said tip means, and a concave distal end portion having a peripheral blunt edge on the other of said tip means. Upon placing a surgical drape between the jaw members of the surgical towel and drape clamp and manipulating the finger loops to close the jaw members the locking ratchets are brought into interengagement with each other, thereby locking the surgical towel and drape clamp in the closed position. At this point the drape is trapped between the blunt distal end portion of the tip means on one of the jaw members and the concave distal end portion of the tip means of the opposing jaw member.

The combination of a blunt distal end portion on the one tip means and the peripheral blunt edge on the concave distal end portion of the other tip means effectively prevents the puncturing, abrading and cutting of the surgical drape or surgical towel while, at the same time, reliably and securely holding the surgical towel or surgical drape.

Figure 1:
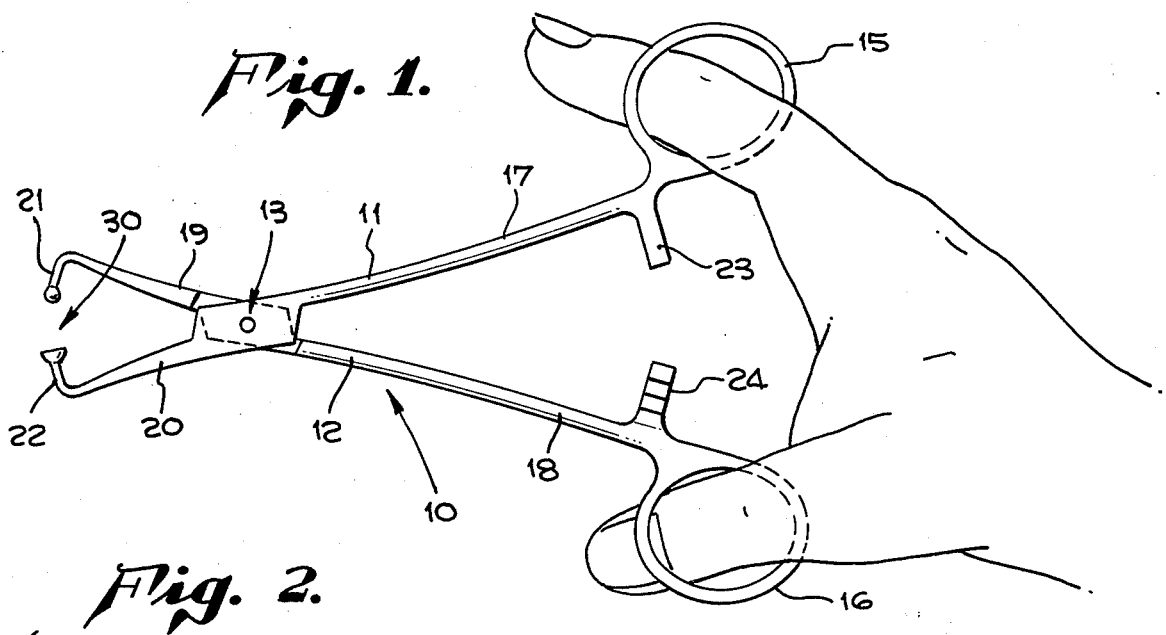
FIG. 1 is a side view showing the improved surgical towel clamp of the present invention in an opened position.
Figure 6:
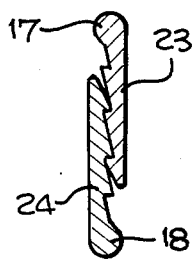
FIG. 6 is a cross sectional view taken through the plane VI—VI of FIG. 3 showing the relationship between the ratchet members which holds the surgical towel and drape clamp of the present invention in a closed position.
Figure 3:
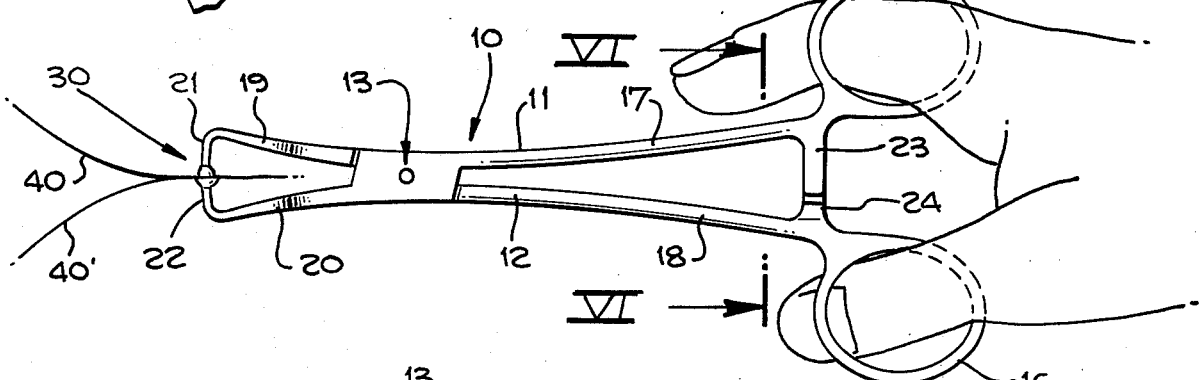
FIG. 3 is a side view showing the improved surgical towel clamp of the present invention in a closed position with a surgical drape or surgical towel trapped between the jaw tip means, said surgical towel clamp being locked in a closed position by ratchet members.
Figure 4:
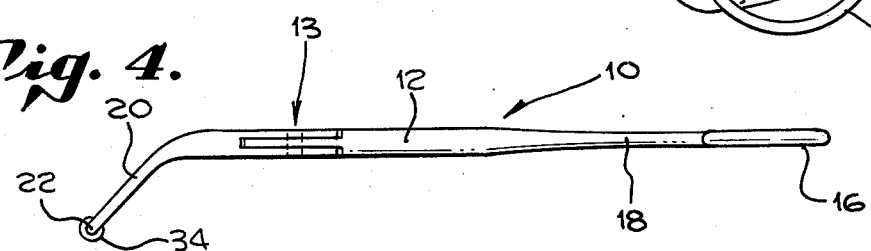
FIG. 4 is an edge view of the surgical towel and drape clamp in a closed position.

DESCRIPTION OF AN EXEMPLARY EMBODIMENT:

Referring firstly to FIG. 1, an exemplary embodiment of a surgical towel and drape clamp in which the improvement of the present invention has been included is indicated generally at 10. The surgical towel and drape clamp has opposing jaw members 19 and 20 which are extended from and operated between the opened and closed positions by the action of shank members 11 and 12 which are pivotally interconnected by rivet 13. Shank members 11 and 12 are reduced in thickness through the regions 17 and 18 and are then formed into finger loops 15 and 16. Locking ratchet members 23 and 24 are positioned such that, upon moving finger loops 15 and 16 toward each other in a closing motion, ratchet members 23 and 24 interlock (FIG. 6) to hold the surgical towel and drape clamp in a closed position (FIG. 3).

Jaw members 19 and 20 are provided with tip means 21 and 22 for holding and clamping surgical towels and drapes. Tip means 21 is shown to have a blunt distal end portion, and tip means 22 is shown to have a concave distal portion.

Figure 2:
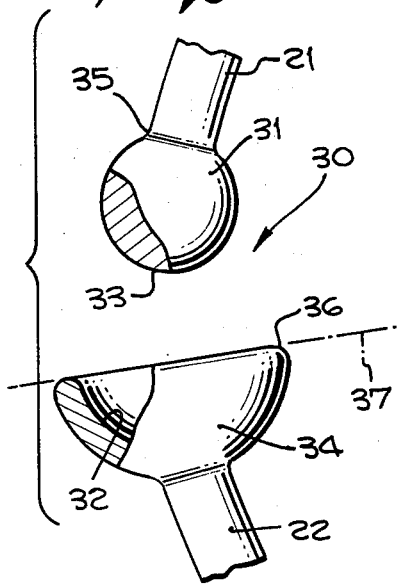
FIG. 2 is a partial side sectional view of the improved jaw tip means of the present invention in an opened position.

The blunt distal end portion of tip means 21 is enlarged at 35 to a generally spherically blunt portion 31 (FIG. 2). The radius of curvature of surface 33 of the generally spherically blunt portion 31 is relatively less than the radius of curvature of concave inner surface 32 of the concave distal end portion 34 of tip means 22. Additionally, concave distal end portion 34 is provided with a peripheral blunt edge 36 (FIG. 2).

Figure 5:
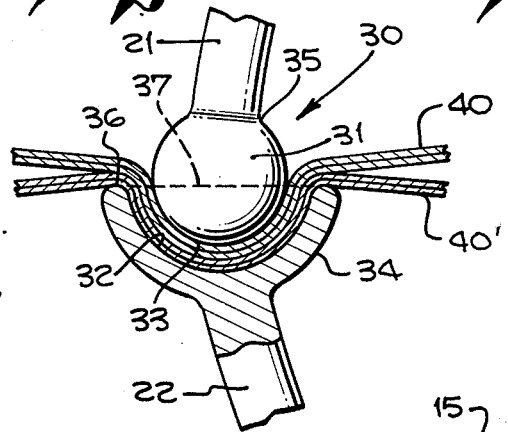
FIG. 5 is a side sectional view showing the relationship between the jaw tip means and a surgical drape or surgical toweling which is trapped therebetween upon closure of said tip means.

The interaction between tip means 21 and 22 and surgical towel or drape material 40 and 40' when the tip means 21 and 22 are in a closed and locked position is shown in FIG. 5. Upon closing and locking of surgical towel and drape clamp 10, the resultant closing and locking of tip means 21 and 22 traps surgical towel or drape material 40 and 40' between the blunt distal end portion of tip means 21 and the concave distal end portion of tip means 22 thereby preventing removal of the surgical towel or drape material from the surgical towel and drape clamp until such clamp is unlocked and opened.

The concave distal end portion 34 of tip means 22 has a planar zone 37 which is defined by the peripheral blunt edge 36 of concave distal end portion 34 and which extends over a concavity which is defined by concave inner surface 32 of the concave distal end portion 34 (FIGS. 2 and 5). The tip means 21 and 22 are so provided that, upon the closing of jaw members 19 and 20 and the associated tip means 21 and 22, the blunt distal end portion of tip means 21 partially penetrates the planar zone 37. Upon penetration of planar zone 37 by spherically blunt distal end portion 31 of tip means 21, the surgical towel or drape material 40 and 40' is trapped within the space defined by planar zone 37 and concave inner surface 32 of concave distal end portion 34 (FIG. 5). It is to be noted that, in addition to the clamping effect of jaw tip means 21 and 22, surgical towel or drape material 40 and 40' is crimped across peripheral blunt edge 36 of concave distal end portion 34. The aforementioned crimping effectively increases the resistance to any displacement of surgical towel or drape material 40 and 40' within surgical towel and drape clamp 10 over the resistance to such movement which would be provided by a clamping action between jaw tip means 21 and 22 alone.

In the exemplary embodiment of the present invention, the blunt distal end portion 31 of tip means 21 is shown to be externally radiused and, in fact, is generally spherical in configuration. Further, the concave distal end portion 34 of tip means 22 is internally radiused and, in fact, is spherically concave. As is shown in FIGS. 2 and 5, upon trapping surgical towel or drape material 40 and 40' between generally spherical distal end portion 31 and generally spherically concave distal end portion 34 of tip means 21 and 22 respectively, no sharp edges or corners are presented to the surgical towel or drape material 40 and 40' thereby eliminating any potential for either puncturing, abrading or cutting the material by the action of jaw tip means 21 and 22.

Further, as was noted prior, the radius of curvature of surface 33 of generally spherical portion 31, the blunt distal end portion of tip means 21, is relatively less than the radius of curvature of concave inner surface 32 of the concave distal end portion 34 of tip means 22. This disparity between the interacting portions of tip means 21 and 22 allows the secure clamping or trapping of any number of thicknesses of surgical towel or drape material, as it allows generally spherical portion 31 of tip means 21 to enter the generally spherically concave portion 32 of concave distal end portion 34 to any extent necessary to trap the material between the tip means 21 and 22. This allows a secure trapping of the material between generally spherical portion 31 and the bottom of concave inner surface 32 in cases where the thickness of material is minimal. This will allow the aforementioned crimping action to take place along with the attendant benefits of such crimping.

I claim:
1. In a surgical towel and drape clamp having opposing jaw members connected to and opened and closed by the action of pivotally interconnected shank members having finger loop members and locking ratchet members and said jaw members further having tip means for holding and clamping surgical drapes, surgical towels and the like, the improvement in said tip means comprising the provision of:
 a blunt hemispheric distal end portion on one of said tip means; and
 a concave hemispheric distal end portion having a peripheral blunt edge on the other of said tip means,
 whereby, upon placing a surgical drape between said tip means and manipulating said finger loops to close said jaw members and locking ratchets, said drape is trapped between said blunt hemispheric distal end portion and said concave hemispheric distal end portion.

2. The improvement in tip means of claim 1, wherein:
 said blunt hemispheric distal end portion is provided with an externally radiused ball-like end portion; and
 said concave hemispheric distal end portion is provided with an internally radiused socket end portion having a relatively larger radius of curvature than that of said ball-like end portion whereby upon trapping a plurality of layers of said surgical drape between said distal end portions of said jaw tip means, a tight clamping is attained while puncturing or cutting of said surgical drape by said jaw tip means is prevented.

* * * * *